United States Patent
Weisman

(10) Patent No.: US 9,138,293 B1
(45) Date of Patent: Sep. 22, 2015

(54) INTRAVASCULAR TREATMENT OF LESIONS USING MAGNETIC NANOPARTICLES

(71) Applicant: Brent Weisman, Beverly Hills, CA (US)

(72) Inventor: Brent Weisman, Beverly Hills, CA (US)

(73) Assignee: Brent Weisman, Beverly Hills, CA (US)

( * ) Notice: Subject to any disclaimer, the term of this patent is extended or adjusted under 35 U.S.C. 154(b) by 0 days.

(21) Appl. No.: 13/952,406

(22) Filed: Jul. 26, 2013

Related U.S. Application Data

(60) Provisional application No. 61/676,749, filed on Jul. 27, 2012.

(51) Int. Cl.
*A61M 37/00* (2006.01)
*A61B 18/18* (2006.01)
*B82Y 5/00* (2011.01)

(52) U.S. Cl.
CPC .............. *A61B 18/18* (2013.01); *A61M 37/00* (2013.01); *B82Y 5/00* (2013.01); *Y10S 977/773* (2013.01); *Y10S 977/908* (2013.01)

(58) Field of Classification Search
USPC ........................................ 600/9, 12; 604/500
See application file for complete search history.

(56) References Cited

U.S. PATENT DOCUMENTS

| | | | |
|---|---|---|---|
| 2005/0090732 A1* | 4/2005 | Ivkov et al. | 600/411 |
| 2005/0271745 A1* | 12/2005 | Gruettner et al. | 424/646 |
| 2006/0041182 A1* | 2/2006 | Forbes et al. | 600/12 |
| 2009/0047318 A1* | 2/2009 | Ludwig et al. | 424/422 |
| 2009/0069741 A1* | 3/2009 | Altshuler et al. | 604/22 |
| 2010/0003197 A1* | 1/2010 | Bikram | 424/9.323 |
| 2010/0204674 A1* | 8/2010 | Forbes et al. | 604/500 |
| 2010/0233147 A1* | 9/2010 | Schwartz et al. | 424/94.64 |
| 2010/0259259 A1* | 10/2010 | Zahn et al. | 324/309 |
| 2011/0071335 A1* | 3/2011 | Ueda et al. | 600/12 |
| 2011/0160515 A1* | 6/2011 | Feucht et al. | 600/10 |
| 2011/0245581 A1* | 10/2011 | Schwartz et al. | 600/12 |
| 2012/0095442 A1* | 4/2012 | Dormer et al. | 604/507 |
| 2012/0232329 A1* | 9/2012 | Creighton | 600/12 |
| 2012/0296149 A1* | 11/2012 | Creighton | 600/12 |

* cited by examiner

*Primary Examiner* — Gerald Landry, II

(74) *Attorney, Agent, or Firm* — Venable LLP; Stefan J. Kirchanski

(57) ABSTRACT

Vascular lesions and plaque can be removed using a treatment based on introduction of magnetic nanoparticles into the circulatory system of a patient having such vascular lesions. The particles in an aqueous suspension are injected near the site of the lesion and magnetic forces are used to immobilize the particles in contact with the lesions. An alternating magnetic field or focused electromagnetic energy is then used to heat the particles, thereby destroying the lesion. Following destruction of the lesion, additional populations of magnetic particles having growth factors, anti-inflammatory agents and other medicaments on their surfaces can be localized at the site of the former lesion. These medicated particles accelerate healing at the site.

9 Claims, No Drawings

INTRAVASCULAR TREATMENT OF LESIONS USING MAGNETIC NANOPARTICLES

CROSS-REFERENCE TO RELATED APPLICATIONS

This application is based on and claims the priority of U.S. Provisional Patent Application 61/676,749 which was filed on 27 Jul. 2012.

BACKGROUND OF THE INVENTION

1. Field of the Invention

The present invention is in the field of medical treatment of arteriosclerosis and related vascular diseases and, more specifically, discloses the use of nanoparticles for the treatment of vascular disease.

2. Description of Related Art

In spite of some improvements in the American diet over the last generation and an increasing popular understanding in the importance of physical activity, heart and vascular disease continue to be major causes of mortality and morbidity. It is common knowledge that "poor" life style including poor diet and lack of adequate physical activity result in clogging of the arteries with a fatty substance known generally as plaque. It would appear that dietary fats contribute to plaque because consumption of "bad" fats such as animal fats, including cholesterol, and chemically synthesized "trans" fats can be directly correlated with plaque formation.

Common non-invasive treatments include dietary modification and use of cholesterol lowering drugs such as statins. Although such treatments are often successful they are not without side-effects. Further, the exact cause of the problem and the reason for the effectiveness of the treatments is not yet completely clear. On one hand there are a number of cultures where individuals consume high fat diets, often containing significant amount of "bad" fats and yet seem to experience few negative consequences. Many of the so-called Mediterranean diet countries seem to avoid many of the worst consequences of a high fat diet; this is the origin of the "French paradox" where consumption of "killer foods" such as foie gras by the French seem to have little negative impact. Of course, the picture is complicated by other factors experienced by most Mediterraneans. Generally, their diets include relatively high amounts of fresh fruits and vegetables as well as plant fats (e.g. olive oil). Mediterraneans generally walk more than Americans and also consume much more red wine than Americans. Thus, it is difficult to pin point which factors in the Mediterranean diet—or rather life style—contribute to vascular health. Even with cholesterol lowering drugs the picture is a bit murky. Although the drugs are generally successful, they seem to be effective even where the patient already has a very low level of cholesterol. There is considerable evidence that many of the cholesterol lowering drugs are potent anti-inflammatory agents. So is the problem with plaque one of excess cholesterol or of systemic inflammation?

Despite their promise non-invasive treatments for vascular disease cannot help all patients. Many individuals are suffering from serious arterial damage at time of diagnosis. Diets and drugs may prevent plaque formation and may even achieve diminution of existing plaque, but a patient with serious plaque build-up may well suffer a fatal heart attack or embolism before drug treatment even has a chance to work. Therefore, invasive procedures are necessary for individuals with significant plaque deposits. The initial treatment for plaque clogged coronary arteries was an auto-graft using the patient's own saphenous veins or other veins to replace the clogged arteries—known as "bypass" surgery. Unfortunately, bypass surgery is incredibly invasive. Often the patient will not even have harvestable veins suitable for a bypass. Balloon angioplasty followed by the placement of a vascular stent has been developed as a less invasive treatment for arterial blockage. However, angioplasty does not remove the plaque and even with a stent present there can be development of a new blockage. Indeed, the damage to the vascular wall caused by the angioplasty and presence of the stent may even stimulate abnormal cell growth which results in vascular stenosis. Clearly, what is needed is additional non-invasive treatment modalities that can actually destroy the plaque and subsequently promote regeneration of the damaged vascular region.

DETAILED DESCRIPTION OF THE INVENTION

The present inventor has been concerned with solving this problem and was encouraged by the use of nanotechnology for other medical treatments. Nanotechnology is an extremely broad technical area and generally deals with materials and devices that are generally in the nanometer size range—that is, usually less than one micrometer. Nanotechnology ranges from the relatively simple such as various materials in the nanometer size range, known as nanoparticles or nanites to the sublimely complex such as nano-machines such as MEMS (micro-electromechanical systems) although most such devices are actually in a micrometer rather than nanometer size range.

At this time there has been more use of nanoparticles in medicine as opposed to use of nano or micro-machines. Nanoparticles often have significantly different properties than larger particles of the same material. This is due, in one instance, to the dramatically greater surface area of nanoparticles on a weight basis. Because red blood cells are about 6-8 micrometers in diameter, it will be appreciated that nanoparticles of 10-50 nanometers (0.01-0.05 micrometers) in diameter are totally dwarfed by the red cells and can readily be distributed in the blood and moved by the blood flow. Therefore, among the first medical uses of nanoparticles has been for the imaging and destruction of cancer cells. Because of their large surface area a wide range of material can be readily chemically linked or adsorbed to the surface of nanoparticles. For example, if antibodies raised against a particular cancer cell or tumor marker are linked to the surface of nanoparticles and these particles are subsequently injected into the vascular circulation, the particles will bind to any cells which react with the antibodies. Depending on the composition of the nanoparticles they can be readily imaged so that the location of the cancer can be located. For example, metallic nanoparticles are readily imaged by imaging technologies depending on x-rays (traditional radiographs as well as CAT scans). Nanoparticles containing certain chemical elements are readily imaged by NMR (nuclear magnetic resonance) technologies such as magnetic resonance imaging (MRI). Additionally, the modified nanoparticles can be used to deliver a payload such as a drug to the cancer cells. Furthermore, metallic particles can be heated by electromagnetic energy so that in theory heat can be specifically delivered to the cancer, to damage the cancer cell. So far, in practice it has proven difficult to deliver a sufficient number of particles to allow ready heat killing of or damage to the cancer cells. This may at least partially due to the limited number of antibody ligands on any one target cell.

Generally, specific antibodies and other specific binding proteins (e.g. lectins) are not useful for targeting and identifying vascular plaque because of the heterogeneous nature of the plaque. Thus, nanoparticles cannot be readily targeted to plaque in the same way they can be targeted to cancer cells. However, unlike the location of small malignancies which might be anywhere in a patient, the location of major plaque deposits can be located using Doppler ultrasound imaging or various radiographic techniques (e.g. angiography). The present invention does not employ nanoparticles to locate a primary plaque lesion; however, once the lesion is located by traditional imaging techniques, a payload of magnetic nanoparticles is introduced into the vicinity of the lesion. By "magnetic" is meant particles that are capable of being moved by a magnetic field (e.g. certain paramagnetic, superparamagnetic, ferromagnetic and ferrimagnetic particles) and generally not particles that are themselves permanent magnets. Introduction of the magnetic nanoparticles is generally in close vascular proximity to the lesion either by means of injection from outside of the body (e.g. by a needle) or delivery through an intravascular catheter threaded through the patient's vascular system to a point near the lesion. Meanwhile, a sufficiently strong magnetic field has been established at the lesion so that when then flowing blood carries the nanoparticles to the lesion, they are immobilized by the magnetic field. The field can be established by permanent magnet or electromagnet devices. Electromagnets are preferred because they can be readily switched on and off and because electromagnetic harnesses can be readily designed which can specifically focus and direct the magnetic field.

The initial purpose is to concentrate the nanoparticles at the site of the lesion. As many particles as possible should be delivered so long as the volume of delivered particles is not great enough to further impact blood flow through the site. In theory the nanoparticles could be introduced into the circulation at any point in the circulatory system because each particle would eventually flow past the lesion and be trapped by the imposed magnetic field. However, the human body has many systems for clearing foreign particles from the circulation so that the point of introduction should be as close to the lesion as practicable to avoid loss of particles. Also, it is desirable to proceed with the treatment as quickly as possible and remote injection of nanoparticles would simply slow down the treatment.

The goal of the treatment is to clear the plaque and restore the artery to its normal condition. Plaque does not simply form as an inert plug. Rather the plaque deposits where the arterial walls are already abnormal or damaged. Thus, optimal treatment really consists of at least two phases. A first phase in which the plaque material is removed and a second phase in which the normal arterial wall is restored.

There are at least two ways in which the magnetic nanoparticles can be used to clear the plaque. The first way takes direct advantage of the ability to heat magnetic particles in situ by applying either a rapidly alternating magnetic field or by focusing electromagnetic energy (in the microwave frequency range) on the site of the particles. In the case of a rapidly alternating magnetic field, the particles are heated by induction heating. In the case of electromagnetic energy a diathermy-like effect occurs. It is also possible to heat the particles with focused ultra-sound. A potential drawback of ultra-sound is its tendency to heat surrounding tissues as well as the particles themselves. If the particles are sufficiently heated, the surface layers of the plaque will be disrupted and dispersed into the circulation as small particles which are subsequently cleared by reticuloendothelial system. In all but the smallest plaques, it is likely that a plurality of heating steps will be necessary to "peel away" the plaque layer by layer. It is not likely that there will be sufficient particle heating to heat a large plaque all the way through, nor would such heating be desirable because it might well damage the living cells in the vessel wall.

The second way takes indirect advantage of heating the particles. For this approach the particles are not simply naked metallic nanoparticles. Instead the metallic nanoparticles are coated with a biologically compatible organic polymer such as albumin. When the particles are heated in contact with the plaque, some of the plaque material becomes absorbed by and/or attached to the organic coating. This results in a wicking-like process that soaks up a portion of the plaque. At that juncture, the magnetic field is released allowing the plaque saturated particles to move with the blood and be cleared by the reticuloendothelial system of the patient. This approach is likely to require repeated injection of fresh particles to completely remove the plaque. Besides providing a coating that helps absorb plaque material, it is also possible to attach surfactants and/or enzymes to the coating to further participate in removal of the plaque. Each successive dose of particles applied is likely to have somewhat different additives.

Once the plaque has been substantially cleared as explained above, the directed nanoparticles can be used to restore the plaque damaged wall of the vasculature. For this purpose drugs (e.g. anti-inflammatories, anticoagulants), growth factors (e.g. vascular endothelial growth factor) and even precursor cells or cellular material (e.g. stem cells and partially differentiated intima cells, etc.) are provided by delivery nanoparticles. Drugs and growth factors can be adsorbed to or linked to a coating on the particles. In the case of cells and cellular material, the delivery particles can be supplied with adsorbed or covalently bound antibodies that bind to specific cellular targets. The linkages between the particles and the antibodies can be readily selected to be cleavable allowing the particles to detach from the delivered cells and cellular material. The delivery particles are introduced close to the site of the partially repaired lesion and held in place by the magnetic field for a sufficient period of time to be effective. The initial goal is to cover the site of the lesion to prevent clot formation. The local introduction of the patient's own stem cells and partially differentiated vascular cells (which can be proliferated in vitro in advance of the treatment) is intended to accelerate the repair process and reduce the time required for the full treatment. It will be appreciated that the requirement for cellular additions is not absolute and will depend on the severity of original vascular damage.

The present invention is ideal for progressive eradication of carotid arterial plaque in a subject with 70%-80% occlusion in the right carotid artery and for whom atherectomy and endarterectomy are contra-indicated. In the case of such a patient with severe blockage in the right carotid artery treatment begins with multiple, staggered administration of nanoparticles en masse into the subject's right carotid artery upstream of the blockage. The nanoparticles may be encapsulated to prevent premature dissipation prior to reaching the occlusion site. At the blockage site the nanoparticles are held in situ via a directed magnetic field, for example from a computer-controlled electromagnetic harness. Directed and focused electromagnetic radiation, most likely in the radio wave or microwave spectrum, or possibly ultra sound/acoustics are then applied to induce nanoparticle hyperthermia, thereby achieving plaque abatement without, damaging surrounding healthy tissue. The plaque-related debris thus generated move into the general circulation and are cleared by the reticuloendothelial network. Carotid stenosis in this hypothetical subject's right carotid artery would have been rendered de minimis after several (perhaps, 10-15) such treatments, which may occur in an out-patient non-surgical setting. The severe perils of invasive remediation attempts will have been avoided.

The present invention can readily deliver drugs, growth factors and cellular materials to damaged vascular areas where plaque is not involved. For example, regions of vascular damage such as aneurysms can benefit from local administration of drugs, etc. by delivery nanoparticles.

The invention claimed is:

1. A method for ameliorating vascular plaque in a vascular circulatory system comprising the steps of:
    introducing magnetic nanoparticles into said circulatory system in proximity to the vascular plaque;
    applying a localized magnetic field to vascular plaque to immobilize the magnetic nanoparticles at the vascular plaque;
    subjecting the vascular plaque to focused electromagnetic radiation to heat the immobilized magnetic particles so that the plaque is disrupted; and
    removing the localized magnetic field to release the magnetic particles.

2. The method according to claim 1 further comprising a step of introducing delivery nanoparticles and immobilization of the delivery nanoparticles at the plaque following the step of subjecting whereby the delivery nanoparticles provide drugs, growth factors or cellular materials that promote healing of the plaque.

3. The method according to claim 1 further comprising using coated magnetic nanoparticles so that the coated nanoparticles absorb the fragments of the disrupted plaque.

4. The method according to claim 1, wherein the steps are repeated at least once so as to disrupt the plaque by degrees.

5. A method for ameliorating vascular plaque in a vascular circulatory system comprising the steps of:
    introducing coated magnetic nanoparticles into said circulatory system in proximity to the vascular plaque;
    applying a localized magnetic field to vascular plaque to immobilize the coated magnetic nanoparticles at and in contact with the vascular plaque;
    subjecting the vascular plaque to focused electromagnetic radiation to heat the immobilized coated magnetic particles the plaque which is and absorbed by or attached to the coated magnetic particles; and
    removing the localized magnetic field to release the magnetic particles.

6. The method according to claim 5, wherein the steps are repeated at least once so as to disrupt the plaque by degrees.

7. The method according to claim 5, wherein said particles are coated with albumin.

8. The method according to claim 5 further comprising a step of introducing delivery nanoparticles and immobilization of the delivery nanoparticles at the plaque whereby the delivery nanoparticles provide drugs, growth factors or cellular materials that promote healing.

9. A method for ameliorating vascular plaque in a vascular circulatory system comprising the steps of:
    introducing coated magnetic nanoparticles into said circulatory system in proximity to the vascular plaque;
    applying a localized magnetic field to vascular plaque to immobilize the coated magnetic nanoparticles at and in contact with the vascular plaque;
    subjecting the vascular plaque to focused radiation to heat the immobilized coated magnetic particles the plaque which is and absorbed by or attached to the coated magnetic particles; and
    removing the localized magnetic field to release the magnetic particles.

* * * * *